(12) United States Patent
Lee

(10) Patent No.: US 8,492,101 B2
(45) Date of Patent: Jul. 23, 2013

(54) CHEMILUMINESCENT ENZYME ASSAY METHOD AND APPARATUS

(75) Inventor: Ji Hoon Lee, Gaithersburg, MD (US)

(73) Assignee: Luminescent MD, LLC, Gaithersburg, MD (US)

( * ) Notice: Subject to any disclaimer, the term of this patent is extended or adjusted under 35 U.S.C. 154(b) by 0 days.

(21) Appl. No.: 12/761,721

(22) Filed: Apr. 16, 2010

(65) Prior Publication Data

US 2011/0045506 A1    Feb. 24, 2011

Related U.S. Application Data

(60) Provisional application No. 61/169,928, filed on Apr. 16, 2009.

(51) Int. Cl.
*G01N 33/53* (2006.01)
*G01N 33/533* (2006.01)

(52) U.S. Cl.
USPC .......................................... 435/7.1; 435/7.92

(58) Field of Classification Search
None
See application file for complete search history.

(56) References Cited

U.S. PATENT DOCUMENTS

| 4,844,966 A | 7/1989 | Calenoff et al. |
| 5,736,320 A | 4/1998 | Schlederer et al. |
| 7,141,677 B2 * | 11/2006 | Lee et al. .................. 548/334.1 |
| 2004/0241767 A1 | 12/2004 | Incaurgarat et al. |

FOREIGN PATENT DOCUMENTS

JP    05111395 A    5/1993

OTHER PUBLICATIONS

Lee et al., "Fast peroxyoxalate chemiluminescence for minimized analytical separation systems," Chem. Commun., 2003, issue 2, pp. 270-271.*

Lee et al., "Solvent and pH effects on fast and ultrasensitive 1,1'-oxalyldi(4-methyl)imidazole chemiluminescence," Analyst, 2003, vol. 128, pp. 1257-1261.*

Luo. L. et al, Talanta, 2007, vol. 72, pp. 1293-1297.

* cited by examiner

*Primary Examiner* — Shafiqul Haq
*Assistant Examiner* — Galina Yakovleva
(74) *Attorney, Agent, or Firm* — Birch, Stewart, Kolasch & Birch, LLP

(57) ABSTRACT

A chemiluminescent enzyme immunoassay method for quantifying antigen or antibody using 1,1'-oxalyldiimidazole (ODI) derivative or 1,1'-oxalyldisodium benzoate (ODB) derivative chemiluminescence (CL) detection was developed. Also, various enzymes were quantified using ODI derivative or DOB derivative CL detection. Fluorescent compound formed from a substrate (non-fluorescent compound) through the enzyme assay methods emitted CL when the fluorescent compound received energy from high-energy intermediate formed in ODI derivative or ODB derivative CL reaction.

2 Claims, 3 Drawing Sheets

CHEMILUMINESCENT ENZYME ASSAY METHOD AND APPARATUS

CROSS REFERENCE TO RELATED APPLICATIONS

This application claims the benefit of U.S. Patent Application No. 61/169,928, which was filed Apr. 16, 2009.

FIELD OF INVENTION

This invention involves chemiluminescent enzyme immunoassays (CLEIAs) capable of quantifying antigen content using 1,1'-oxalyldiimidazole (ODI) derivative or 1,1'-oxalyldisodium benzoate (ODB) derivative chemiluminescence (CL) detection.

BACKGROUND

Even though radioimmunoassay (RIA) developed in 1960 is applied to quantify trace levels of biomolecules (e.g., hormone, tumor markers) the use of isotope molecules tagged antigen or antibody has various problems related to stability of labeled biomarkers (e.g., short half-life, radiolysis) and safety (e.g., laboratory personnel, waste, the requirement of building special laboratory facilities).

In order to solve the problems occurring from RIA, enzyme immunoassay (EIA) methods capable of quantifying various biomarkers with an enzyme rather than radioactivity as the reporter label were developed with various detections. Sensitivity of EIA depends on the physical properties of applied detection method such as colorimeter, fluorescence, and chemiluminescence. EIA with chemiluminescence detection using luminol or 1,2-dioxetane is much more sensitive than other immunoassays including RIA. Also, the sensitivity of chemiluminescence EIA (CLEIA) is better than those of chemiluminescence immunoassay (CLIA) using acridinium ester- or Ruthenium chelate-labeled antigen or antibody. Thus, CLEIA is widely applied to quantify toxic biomolecules and drugs as well as to diagnose various diseases. However, applications of CLEIA commercialized in the current market aren't as wide as those of fluorescence EIA. This is because luminol and 1,2-dioxetane derivatives widely applied as a CL substrate under CLEIA only react with a specific label enzyme. For example, CLEIA using luminol is applied when luminol reacts with antigen or antibody labeled with horseradish peroxidase (HRP) for 15~60 minutes. In the case of CLEIA using 1,2-dioxetane derivatives, maximum CL is measured when 1,2-dioxetane and antigen or antibody conjugated to alkaline phosphatase (ALP) are incubated for 5~60 minutes.

It is well-known that peroxyoxalate chemiluminescence (POCL) detection is much more sensitive and selective than other CL detections. Unfortunately however, due to the instability of POCL reagents (e.g., bis(2,4-dinitrophenyl) oxalate (DNPO), bis(2,4,6-thrichlorophenyl) oxalate (TCPO)) in aqueous solution, it is difficult to apply POCL detection in CLEIA.

Recently, 1,1'-oxalyldiimidazole (ODI) derivatives' and 1,1'-oxalyldisodium benzoate (DOB) derivatives[2] were synthesized as new POCL reagents. Trace levels of fluorescent biomolecules dissolved in aqueous solution were quantified using the new POCL reagents, based on the reaction mechanism shown in Scheme 1 and 2, even though they are also unstable in aqueous solution. This was possible because the reaction between $H_2O_2$ and ODI or ODB is faster than their decomposition in aqueous solution. Using the chemical and physical properties of the new POCL reagents, novel CLEIA was developed. The sensitivity of this CLEIA was better than that of currently applied CLEIA. Also, the applications of CLEIA using ODI or ODB derivatives were as wide as those of fluorescence EIA because low concentrations of antigen or antibody conjugated to various enzymes including HRP and ALP were quantified under the novel CLEIA.

Scheme 1. Reaction mechanism of ODI derivative CL.

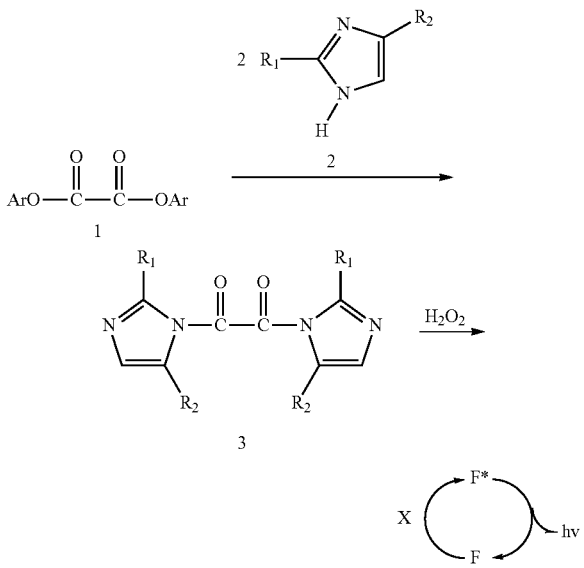

1: oxalate esters (e.g., DNPO, TCPO), 2: Imidazole derivatives (When $R_1$ is H, $CH_3$, or $CH_2CH_3$, $R_1$ is H. Or when $R_2$ is H or $CH_3$, $R_1$ is H.), 3: ODI derivative, X: high-energy intermediate, F: fluorescent compound Scheme 2. Reaction mechanism of ODB derivative CL.

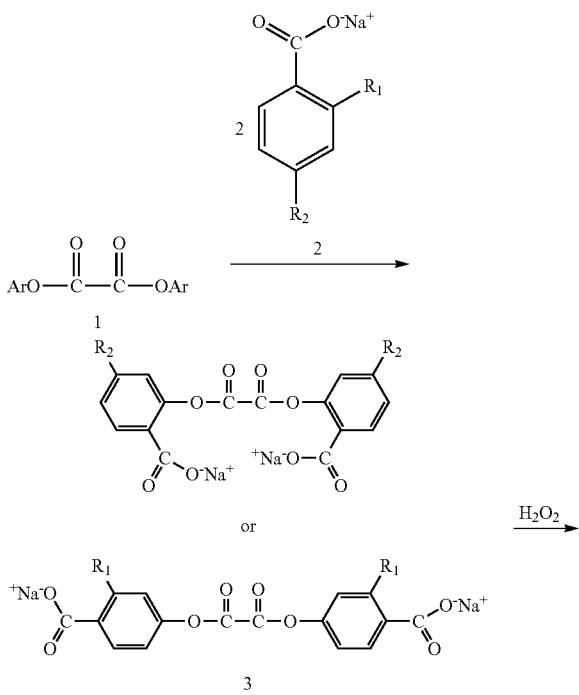

-continued

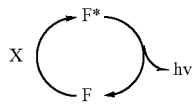

1: oxalate esters (e.g., DNPO, TCPO), 2: N-hydroxy benzoic acid sodium salt derivatives (When $R_1$ is OH, $R_2$ is H. Or when $R_2$ is OH or $CH_3$, $R_1$ is H.), 3: ODI derivative, X: high-energy intermediate, F: fluorescent compound

SUMMARY

The present invention provides a chemiluminescent enzyme immunoassay method for the quantification of antigen using ODI derivative or ODB derivative CL detections. The method of this invention provides an accurate, fast, precise, reproducible and simple way to quantify biomarkers (e.g., proteins, cells) using enzyme-conjugated antigen or enzyme-conjugated antibody, and gene product mutations using single nucleotide polymorphisms (SNPs). According to one of several embodiments of the invention, a fluorescent compound can be linked directly to an antibody or antigen of interest, or it can be linked indirectly via a secondary (detection) antibody and an enzyme and appropriate substrate. Alternatively, quantum dots also can be used to signal the presence of an antigen, antibody, or mutation of interest.

DETAILED DESCRIPTION

Figure 1:
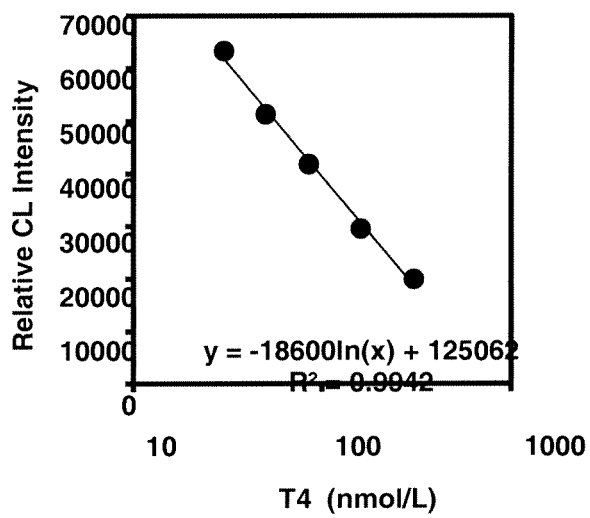
FIG. 1 shows a calibration curve which quantifies total T4 in CLEIA using T4-HRP conjugate and OD4MI CL detection.

The present invention is enzyme immunoassay (EIA) method using ODI or ODB derivative CL detection capable of quantifying biomarkers (e.g., gene, protein, cell) widely applied to diagnose various diseases (e.g., cancer, cardiac aliment, diabetes, infectious diseases, thyroid) and analyze toxic materials and drugs.

In the CLEIA method of the present invention, the surface of polystyrene strip wells or magnetic beads is coated with a monoclonal primary antibody of an antigen of interest. The magnetic beads are diluted using assay buffer solution in borosilicate glass test tubes (10×75 mm).

Standard and test samples are prepared. Standard samples are references in which the quantity of antigen in the sample is known, whereas test samples are samples in which the quantity of antigen in the sample is to be determined. Appropriate volume (20~50 µl) of standard and test samples were inserted into each polystyrene strip well or each test tube.

In order to observe sandwich CLEIA, 50~100 µl detection antibody-labeled HRP or ALP is added into each polystyrene strip well or each test tube. In the case of competitive CLEIA, 50~100 µl antigen-labeled HRP or ALP is added into each polystyrene strip well or test tube.

The polystyrene strip wells or test tubes are mixed for a short period of time and incubated for an appropriate amount of time (15~30 minutes). All unbound material on the surface of polystyrene strip well or magnetic bead are removed by washing it with washing buffer solution. The magnetic beads in the test tube are washed with a magnetic separator.

100~200 µl HRP-substrate (e.g., Amplex Red, 2,3-diaminophenazine (DAPN)) solution containing $H_2O_2$ or 100~250 µl ALP-substrate (e.g., fluorescein diphosphate (FDP), 4-methyl umbelliferyl phosphate (MUP), 3-O-methyl fluorescein phosphate) dissolved in various buffer solutions are added into each polystyrene strip tube or each test tube. The polystyrene strip tubes and test tubes are incubated for 1.0~15 minutes. The incubation time is dependent on the reaction activity between enzyme conjugated to an antigen or antibody and enzyme-substrate.

After the incubation, the solution in each polystyrene strip tube or each test tube is transferred into a 0.5 ml centrifuge tube. 10 µl of solution transferred into the centrifuge tube is added into a polypropylene 96-well plate or a borosilicate glass test tube (12×75 mm).

The polypropylene 96-well plate is input to a microplate reader with a CL detection and two dispensers. The glass test tube is input to a luminometer with two dispensers. A 40 ml vial containing $H_2O_2$ dissolved in isopropyl alcohol is connected to a dispenser. A 40 ml vial containing ODI or ODB is connected to the other dispenser. Finally, CL emitted in each well or test tube was measured when 25 µl $H_2O_2$ and 25 µl ODI or ODB were added into each well through the dispensers.

Based on CL emissions measured in the presence of wide concentrations of standard samples, a calibration curve (x axis: concentration of sample, y axis: CL intensity) is plotted. The concentration of test sample is determined using the calibration curve and CL emission measured in the presence of each test sample.

EXAMPLES

Reagents and Kits

Chemicals: Bis(2,4,6-trichlorophenyl)oxalate (TCPO), Imidazole (ImH), 2-Methylimidazole (2MImH), 2-Ethylimidazole (2EImH), 4-Methylimidazole (4MImH), o-phenylenediamine (OPDA), 30% Hydrogen peroxide ($H_2O_2$), 4-Hydroxybenzoic acid sodium salt, $MgCl_2$, and $CaCl_2$ were purchased from Sigma-Aldrich. Ethyl acetate (HPLC grade), Isopropyl alcohol (HPLC grade), deionized water (LC-MS grade), and Dimethylsulfoxide (DMSO) were purchased from EMD chemicals. Amplex Red was purchased from Biotium. Fluorescein diphosphate, tetraammonium salt (FDP) and 4-methyl umbelliferyl phosphate (MUP) were purchased from AnaSpec. 0.1 M sodium phosphate EDTA buffer solution (pH 7.4) was purchased from Teknova. Sterile human serum was purchased from Rockland Immunochemicals. Thyroid panel (Triidothyronine (T3), Thyroxine T4, Thyroid Stimulating Hormone (TSH)), Prostate Specific Antigen (PSA), and Carcinoembryonic Antigen (CEA) as one of AccuLite® CLIA kits applied with luminol CL detection was purchased from Monobind. Total human serum T4 EIA kit and Human TSH EIA kit were purchased from Immunometrics (UK) Ltd. 1,2-dioxetane and luminol CL reagents prepared under optimum condition were purchased from KPL.

Instruments

In order to measure light under various CLEIA conditions, Luminoskan Ascent with two dispensers (Thermo Scientific) and LB 9507 Luminometer with two dispensers (Berthold Technologies) were used.

Example 1

Competitive CLEIA Procedure

A. Quantification of Total T4 Using T4-HRP Conjugate and ODI Derivative CL Detection Preparation AccuLite® CLIA kit capable of quantifying T4 with luminol CL detection was used to develop new CLEIA method using ODI derivative CL detection. The kit is composed of 96 strip wells coated with streptavidin, T4-HRP conjugate, T4 antibody-labeled biotin, luminol as a substrate, reaction buffer, and washing buffer.

6 different T4 serum samples (0, 30, 50, 85, 160, 305 nmole/L), components of Total Human Serum T4 EIA kit, were used as standard samples.

As a substrate for ODI derivative CL detection, 50 μM Amplex Red reagent containing 2.0 mM $H_2O_2$ in deionized water was prepared. The working solution was prepared with the following components;

25 μl of 10 mM Amplex Red stock solution prepared with DMSO.

500 μl of 20 mM $H_2O_2$ prepared in deionized water.

4.475 ml deionized water.

1,1'-Oxalyldi-4-methyl-imidazole (OD4MI), one of ODI derivatives was formed from the reaction between 5.0 μM TCPO, and 10.0 μM 4-Methylimidazole (4MImH) in Ethyl acetate. 100 mM $H_2O_9$ was prepared in Isopropyl alcohol.

Another ODI derivative (e.g., 1,1'-Oxalyldiimidazole (ODI), 1,1'-Oxalyldi-2-methyl-imidazole (OD2MI), 1,1'-Oxalyldi-2-ethyl-imidazole (OD2EI)) were formed from the reaction between 5.0 μM TCPO and 10.0 μM a imidazole derivative (e.g, ImH, 2MImH, 2EImH) in Ethyl acetate.

Procedure

1. Pipette 25 μl of the serum T4 standard and test samples into the assigned strip wells coated with primary antibody for T4, which is a component of AccuLite® CLIA kit.
2. Add 50 μl of T4-HRP conjugate to each strip well containing serum standard or test sample
3. Add 50 μl of T4 antibody conjugated to biotin to each strip well.
4. Swirl the strip wells for 20 seconds.
5. Incubate for 20 minutes at 37° C.
6. Discard the contents of each strip well.
7. Wash each plate with 300 μl washing buffer. Repeat four additional times.
8. Add 100 μl working solution containing 50 μM Amplex Red and 2.0 mM $H_2O_2$ to each strip well.
9. Incubate for 5 minutes at room temperature (21~23° C.) in the dark.
10. Transfer the working solution (100 μl) in each strip well into a 0.5 ml centrifuge tube.
11. Pipette 10 μl of working solution into the assigned test tube (12×75 mm) or strip well. Store the rest in 0.5 ml centrifuge tube in a refrigerator (4° C.)
12. Insert the test tube into a luminometer or the strip well into a microplate luminometer.
13. Read CL emitted when OD4MI and $H_2O_2$ are added into the test tube or strip well through two dispensers.

Scheme 3 ODI CLEIA using HRP-conjugated antigen or antibody and Amplex Red as a substrate.

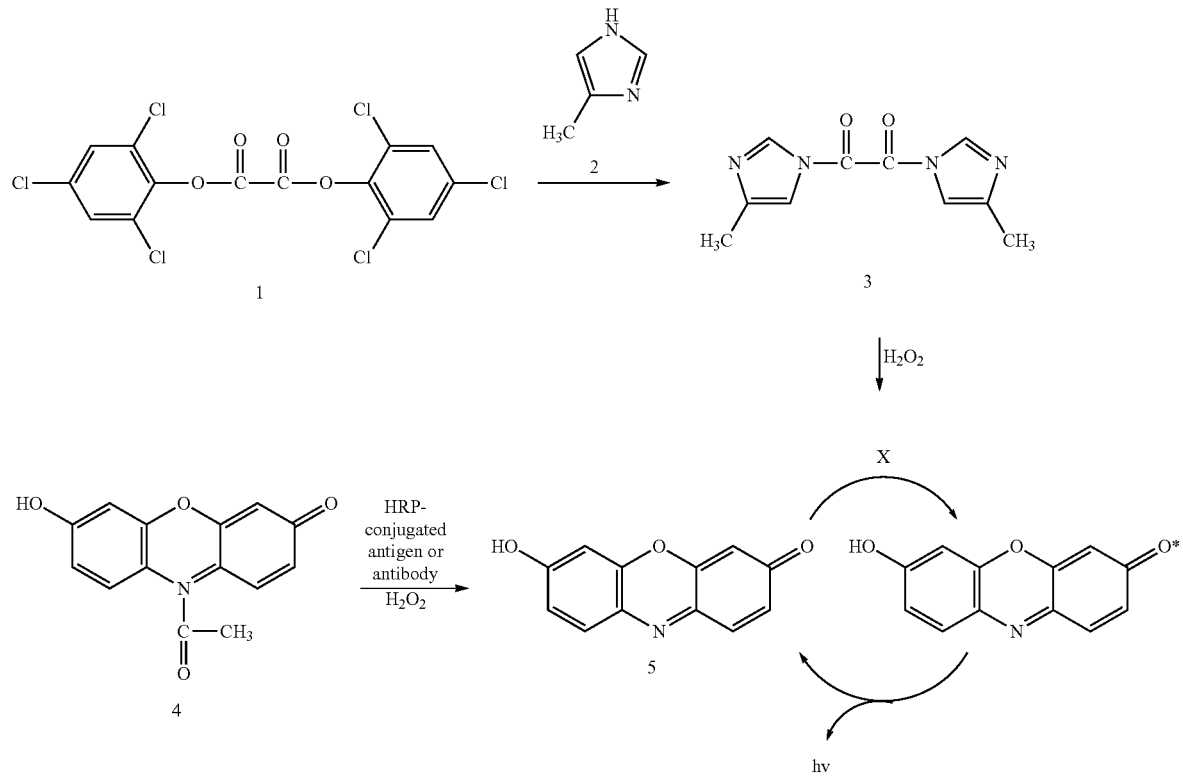

1 TCPO, 2 4-methylimidazole (4MImH), 3 ODI, 4 Amplex Red, 5 Resorufin, X high-energy intermediate Resorufin is formed from the reaction of HRP and Amplex Red in the presence of $H_2O_2$. The fluorescent product Resorufin is excited when high-energy intermediate (X), formed from the reaction between OD4MI and $H_2O_2$, transfers energy to resorufin. And then, the excited resorufin emit strong CL (see Scheme 3).

As shown in FIG. 1, the calibration curve having good $R^2$ was obtained under a wide concentration range of T4. The dynamic range (30~305 nmol/L) under OD4MI CL detection was wider than that ($R^2$ in the range of 30~305 nmol/L=0.978) under luminol CL detection obtained with the commercialized immunoassay kit (AccuLite® CLIA kit for quantifying total T4). Also, the incubation time (25 minutes) of the mixture (T4, T4-HRP conjugate, and T4 antibody-biotin conjugate) in the strip well under OD4MI CL detection is much shorter than that (45 minutes) under luminol CL detection. Also, the limit of detection (LOD=the measurement of zero dose−2 standard deviations=1.6 nmol/L) under OD4MI CL detection was 2 times lower than that (3.3 mmol/L) under luminol CL detection.

The dynamic range of 30~160 nmol/L ($R^2$=0.994) of calibration curve was obtained when the incubation time between HRP and Amplex Red in the presence of $H_2O_2$ (see the number 9 of procedure described above.) was 1 minute. The dynamic range was shorter than that obtained at 5 minutes of incubation time. LOD under the former was the same as that under the latter within statistical error range (95% confidence interval). This result indicates that the sensitivity of OD4MI CLEIA is dependent on the incubation time between HRP and Amplex Red in the presence of $H_2O_2$. Based on the experimental results, the dynamic range of 50~305 nmol/L ($R^2$ in the range of 50~305 nmol/L=0.990) was obtained when the incubation time between HRP and Amplex Red in the presence of $H_2O_2$ was increased up to 30 minutes. This result indicates that it is possible to sense low concentration of HRP with the increase of incubation time. However, it was impossible to sense relatively high concentration of HRP because CL emission of relatively high concentration of resorufin, formed from the reaction between HRP and Amplex Red in the presence of $H_2O_2$, is decreased due to the self quenching of resorufin.

The sensitivity of CLEIA with ODI derivative CL detection was dependent on the properties of ODI derivatives (e.g. OD1, OD2MI, OD2EI, OD4MI). The sensitivity of CLEIA with OD4MI CL detection was better than those with other ODI derivative CL detection (OD4MI>ODI>OD2EI>OD2MI).

TABLE 1

Linearity of T4 OD4MI CLEIA results on sample dilution (n = 8)

| Dilution Factor | Measured T4 (nmol/L) | Recovery (%) |
|---|---|---|
| 1:1 | 250.0 | — |
| 1:2 | 244.8 | 97.9 |
| 1:4 | 253.5 | 101.4 |
| 1:8 | 247.7 | 99.1 |

The T4 test sample (250.0 nmol/L) was prepared with a T4 standard sample (305 nmol/L) and human serum not containing T4. The T4 test sample were diluted 1:2, 1:4, and 1:8 using the same human serum. The measured T4 values shown in Table 1 were obtained with multiple of the dilution factor. Table 1 shows the good linearity for percent recoveries obtained with the dilution of test sample.

B. Quantification of Total T4 Using T4-ALP Conjugate and ODI Derivative CL Detection Preparation Total Human Serum T4 EIA kit capable of quantifying total T4 in human serum with an optical density detection was applied to develop new CLEIA method using ODI derivative CL detection. The kit contains 6 different T4 standards (0~305 nmol/L), blocking reagent, a mouse monoclonal anti-T4 antibody, T4 conjugated to Alkaline phosphatase (ALP), anti-IgG antibodies linked to magnetic particles, assay buffer (0.25 M Tris/HCl buffer pH 8.0 containing BSA, magnesium and zinc chloride and sodium azide), and washing buffer (0.25 M Tris/HCl buffer pH 7.4 containing BSA, magnesium and zinc chloride and sodium azide).

30 μM FDP dissolved in the phosphatase assay buffer (50 mM Tris-HCl, 0.1 mM $CaCl_2$, pH 7.0) was prepared as a substrate for ODI derivative CL detection.

1,1'-Oxalyldi-4-methyl-imidazole (OD4MI), one of ODI derivatives was formed from the reaction between 5.0 μM TCPO and 10.0 μM 4-Methylimidazole (4MImH) in Ethyl acetate. 100 mM $H_2O_2$ was prepared in Isopropyl alcohol.

Procedures

1. Pipette 25 μl standard or test sample into a test tube (10×75 mm).
2. Add 50 μl of T4 blocking reagent to the test tube.
3. Add 50 μl of T4-labeled ALP to the test tube.
4. Add 50 μl of monoclonal anti-T4 antibody to the test tube.
5. Cover the test tube and briefly vortex mix.
6. Incubate the tube at 37° C. for 10 minutes.
7. Add 50 μl of anti-IgG antibodies kinked to magnetic particles.
8. Cover the test tube and briefly vortex mix.
9. Incubate the tubes at 37° C. for 25 minutes.
10. Decant the supernatant liquid form each tube after separating magnetic beads using an appropriate magnetic base (e.g., magnetic bar or magnetic holder).
11. Wash the magnetic beads using washing buffer and the magnetic base. Repeat 2 additional times.
12. Add 250 μl of 30 μM FDP to the test tube.
13. Cover the tube and briefly vortex mix.
14. Incubate the tube at 37° C. shaking slowly for 10 minutes in the dark.
15. Transfer the solution (250 μl) to a centrifuge tube after the separation of magnetic beads using the magnetic base.
16. Pipette 10 μl of working solution into the assigned test tube (12×75 mm) or strip well. Store the rest in 0.5 ml centrifuge tube in a refrigerator (4° C.)
17. Insert the test tube into a luminometer or the strip well into a microplate luminometer.
18. Read CL emitted when OD4MI and $H_2O_2$ are added into the test tube or strip well through two dispensers.

Scheme 4 ODI CLEIA using ALP-conjugated antigen or antibody and FDP as a substrate

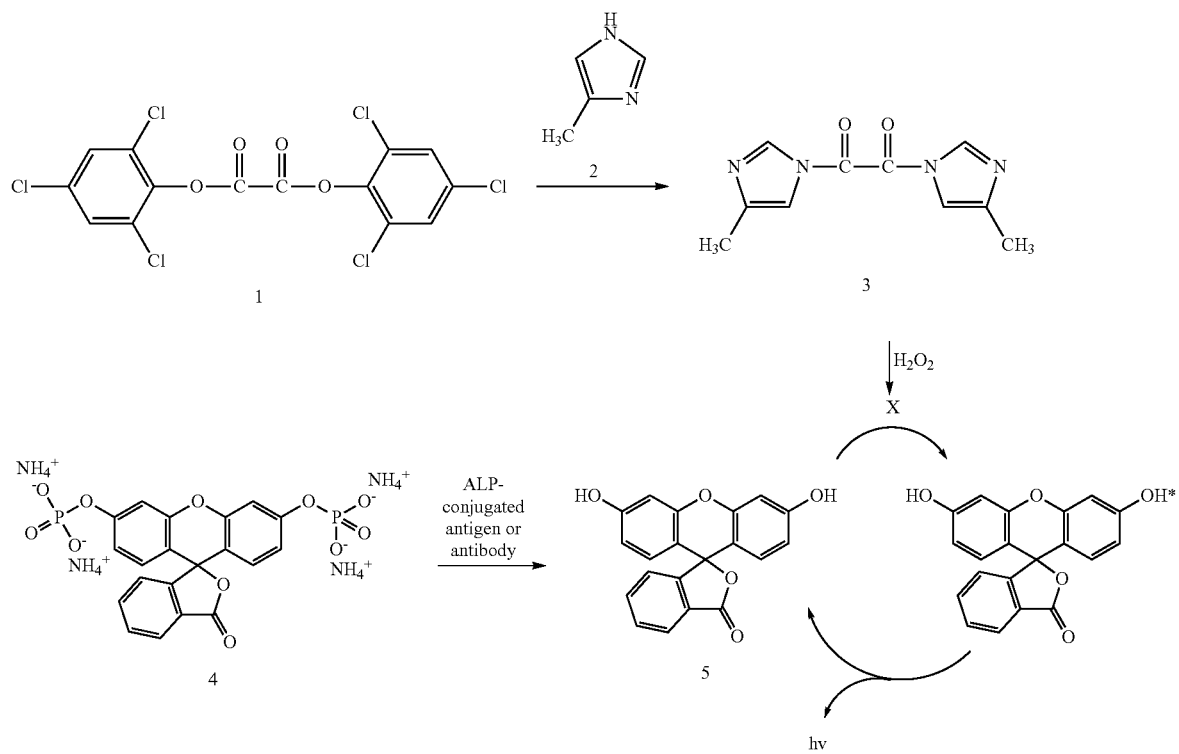

1 TCPO, 2 4-methylimidazole (4MImH), 3 ODI, 4 FDP, 5 fluorescein, X high-energy intermediate Fluorescein is formed from the reaction of ALP and FDP. The fluorescent product Fluorescein is excited when high-energy intermediate (X), formed from the reaction between OD4MI and $H_2O_2$, transfers energy to DAPN. And then, the excited Fluorescein emit strong CL (see Scheme 4).

Figure 2:
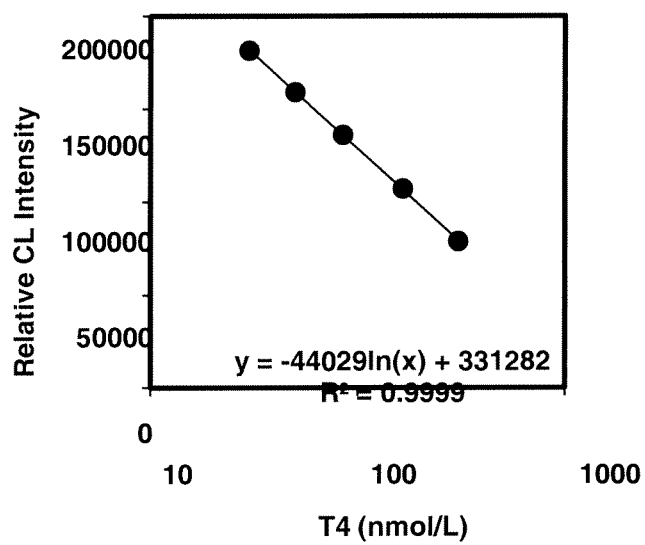
FIG. 2 shows a calibration curve to quantify total T4 in CLEIA using T4-ALP conjugate and OD4MI CL detection.

As shown in FIG. 2, the calibration curve having good $R^2$ was obtained under the wide concentration range of T4. The dynamic range (30~305 nmol/L) of CLEIA capable of quantifying T4 using ALP and OD4MI CL detection (FIG. 2) was the same as that capable of quantifying T4 using HRP and OD4MI CL detection (FIG. 1). The sensitivity (LOD) of the former is also similar to that of the latter within statistical error range (95% confidence interval) even though the optimum incubation time between T4-linked ALP and FDP to obtain FIG. 2 was longer than the optimum incubation time between T4-conjugated HRP and Amplex Red in the presence of $H_2O_2$ to observe FIG. 1.

TABLE 2

Linearity of T4 OD4MI CLEIA results on sample dilution (n = 8)

| Dilution Factor | Measured T4 (nmol/L) | Recovery (%) |
|---|---|---|
| 1:1 | 250.0 | — |
| 1:2 | 240.8 | 96.3 |
| 1:4 | 252.7 | 101.1 |
| 1:8 | 257.9 | 103.2 |

The T4 test sample (250.0 nmol/L) was prepared with a T4 standard sample (305 nmol/L) and human serum processed in the T4 OD4MI CLEIA. The T4 test sample were diluted 1:2, 1:4, and 1:8 using the same human serum. The measured T4 values shown in Table 2 were obtained with multiple of the dilution factor. The linearity for percent recoveries obtained with the dilution of test sample shown in Table 2 was as good as that shown in Table 1.

In conclusion, these results indicate that ODI derivative CL detection can be applied to quantify various enzymes (e.g., HRP, ALP) with appropriate substrates (e.g, Amplex Red, OPDA, FDP, MUP, 3-O-methyl fluorescein phosphate).

Example 2

Sandwich CLEIA Procedure

A. Quantification of TSH Using TSH Detection Antibody-HRP Conjugate and ODI Derivative CL Detection or ODB Derivative CL Detection Preparation AccuLite® CLIA kit capable of quantifying TSH with luminol CL detection was used to develop new CLEIA method using ODI derivative CL detection. The kit is composed of 96 strip wells coated with monoclonal TSH primary antibody, TSH detection antibody-HRP conjugate, luminol as a substrate, reaction buffer, and washing buffer.

6 different TSH serum samples (0, 0.5, 2.5, 10, 20, 40 μIU/ml), components of AccuLite® CLIA kit, were used as standard samples.

50 μM Amplex Red reagent containing 2.0 mM $H_2O_2$ in deionized water were prepared as described in Example 1 (A).

As another substrate for ODI derivative CLEIA, 0.25 mg/ml OPDA containing 20 mM $H_2O_2$ in deionized water.

OD4MI was formed from the reaction between 5.0 μM TCPO and 10.0 μM 4-Methylimidazole (4MImH) in Ethyl acetate. 100 mM $H_2O_2$ was prepared in Isopropyl alcohol.

As another CL reagent, 1,1'-oxalyldisodium benzoate (ODB) derivatives (e.g., 1,1'-oxalyldi-2-sodiumbenzoate (OD2B), 1,1'-oxalyldi-4-sodiumbenzoate (OD4B)) were formed from the reaction between 0.5 mM TCPO and 1.0 mM 2-hydroxybenzoic acid sodium salt or 4-Hydroxybenzoic acid sodium salt in Ethyl acetate. 100 mM $H_2O_2$ was prepared in Isopropyl alcohol.

Procedures

1. Pipette 50 μl of TSH standard or test sample into a strip well.
2. Add 100 μl of TSH detection antibody-HRP conjugate to the strip well
3. Swirl the strip wells for 20 seconds.
4. Incubate for 20 minutes at 37° C.
5. Discard the contents of each strip wells.
6. Wash each plate with 300 μl washing buffer. Repeat four additional times.
7. (a) Add 100 μl working solution containing 50 μM Amplex Red and 2.0 mM $H_2O_2$ to each strip well. Or, (b) add 100 μl working solution containing 0.5 mg/ml OPDA and 20 mM $H_2O_9$ to each well.
8. (a) For the working solution containing 50 μM Amplex Red and 2.0 mM $H_2O_2$, incubate for 1 minute 30 seconds at room temperature (21~23° C.) in the dark. (b) For the working solution containing 50 μM Amplex Red and 2.0 mM $H_2O_2$, incubate 10 minutes at room temperature (21~23° C.) in the dark.
9. Transfer the working solution (100 μl) in each strip well into a 0.5 ml centrifuge tube.
10. Pipette 10 μl of working solution into the assigned test tube (12×75 mm) or strip well. Store the rest in 0.5 ml centrifuge tube in a refrigerator (4° C.).
11. Insert the test tube into a luminometer or the strip well into a microplate luminometer.
12. (a) Read (integration time: 0.5 seconds) emitted CL for 0.5 seconds when OD4MI and $H_2O_2$ are added into the test tube or strip well through two dispensers. (b) Read emitted CL for 2.0 seconds when ODB derivative and $H_2O_2$ are added into the test tube or strip well through two dispensers.

Figure 3:
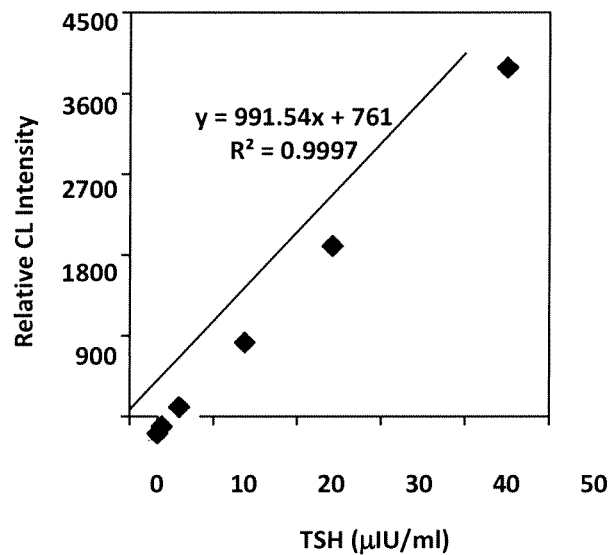
FIG. 3 shows a calibration curve to quantify total TSH in CLEIA using TSH detection antibody-HRP conjugate and OD4MI CL detection.

A-1. Quantification of TSH in CLEIA Using OD4MI CL Detection and Amplex Red in the Presence of $H_2O_2$ as a Substrate As shown in FIG. 3, the calibration curve having good $R^2$ was obtained under the wide concentration range of TSH. The dynamic range (0~40 μIU/ml) under OD4MI CL detection was the same as that ($R^2$ in the range of 0.5~40 μIU/ml=0.994) under luminol CL detection obtained with the commercialized immunoassay kit (AccuLite® CLIA kit for quantifying TSH). However, the total incubation time (21 minute 30 seconds) of the mixture in the strip well under OD4MI CL detection is 2.33 times shorter than that (50 minutes) under luminol CL detection. Also, LOD (the measurement of zero dose+2 standard deviations=0.05 μIU/ml) under OD4MI CL detection was about 2 times lower than that (0.09 μIU/ml) under luminol CL detection.

With the increase of the incubation time, it was possible to determine lower LOD than 0.05 μIU/ml. However, it was impossible to quantify relatively high concentration of TSH because CL emission of relatively high concentration of resorufin, formed from the reaction between HRP and Amplex Red in the presence of $H_2O_2$, is decreased due to the self quenching of resorufin.

A-2. Quantification of TSH in CLEIA Using OD4MI CL Detection and OPDA in the Presence of $H_2O_2$ as a Substrate 2,3-diaminopherazine (DAPN) is formed when HRP reacts with OPDA in the presence of $H_2O_2$. The fluorescent product DAPN are excited when high-energy intermediate, formed from the reaction between OD4MI and $H_2O_2$, transfers energy to DAPN. And then, the excited DAPN emit strong CL (see Scheme 1).

Based on the Schemes 1, low concentration of TSH in human serum was determined using OD4MI CLEIA capable of quantifying DAPN formed from the reaction between TSH detection antibody-HRP conjugate bound with TSH and OPDA in the presence of $H_2O_2$ for 10 minutes (see #9 of the procedures described above). The calibration curve of 0.5~40 μIU/ml ($R^2$ in the range of 0.5~40 μIU/ml=0.992) was obtained. However, the LOD (0.2 μIU/ml) in OD4MI CLEIA with OPDA wasn't as good as that (0.05 μIU/ml) with Amplex Red in spite of the long incubation between TSH detection antibody-HRP conjugate bound with TSH and OPDA in the presence of $H_2O_2$. This is because quantum efficiency of OPDA is lower than that of Amplex Red.

The results in this research indicate that fluorescent products formed from the reaction between HRP and various substrates in the presence of $H_2O_2$, could be applied to CLEIA with OD4MI CL detection.

A-3. Quantification of TSH in CLEIA Using ODB Derivative CL Detection and Amplex Red in the Presence of $H_2O_2$ as a Substrate Using OD4B instead of ODI derivatives, low concentration of TSH was quantified in CLEIA with TSH detection antibody-HRP conjugate and Amplex Red in the presence of $H_2O_2$. Relative CL intensity measured in OD4B CL detection was 10 times lower than that in ODI derivative CL detection even though the concentration of TCPO used to produce OD4B were 100 times higher than that to form ODI. However, the background noise of the former was about 20 times lower than that of the latter. Due to the properties of OD4B CL, the integration time (2 seconds) of light emitted in OD4B CLEIA was 4 times longer than that in OD4MI CLEIA. Based on the experimental condition of OD4B CLEIA, the LOD (0.04 μIU/ml) and dynamic range (0~40 μIU/ml, $R^2$=0.998) determined in CLEIA with ODB derivative CL detection were was similar to or the same as those (see Example 2-A-1) obtained with ODI derivative CL detection within the statistical error range (95% confidence interval).

The sensitivity of CLEIA with ODB derivative CL detection was dependent on the properties of ODB derivatives. The LOD of CLEIA with OD4B CL detection was about 3 times lower than that with OD2B CL detection.

B. Quantification of TSH Using TSH Detection Antibody-ALP Conjugate and ODI Derivative CL Detection Preparation Total Human Serum TSH EIA kit capable of quantifying TSH in human serum with an optical density detection was applied to develop new CLEIA method using ODI derivative CL detection. The kit is composed of magnetic beads coated with monoclonal TSH primary antibody, TSH detection antibody-ALP conjugate, assay buffer, and washing buffer.

6 different TSH serum samples (0, 0.5, 2.5, 10, 20, 40 μIU/ml), components of AccuLite® CLIA kit, were used as standard samples.

As substrates for ODI derivative CL detection, 30 μM FDP and 70 μM MUP dissolved in the phosphatase assay buffer (50 mM Tris-HCl, 0.1 mM $CaCl_2$, pH 7.0) were prepared.

1,1'-Oxalyldi-4-methyl-imidazole (OD4MI), one of ODI derivatives was formed from the reaction between 5.0 μM TCPO and 10.0 µM 4-Methylimidazole (4MImH) in Ethyl acetate. 100 mM $H_2O_2$ was prepared in Isopropyl alcohol.

Procedures

1. Pipette 50 µl TSH standard or test sample into a test tube (10×75 mm).
2. Add 50 µl of magnetic beads linked to monoclonal TSH primary antibody to the test tube.
3. Add 250 µl of TSH detecting antibody-labeled ALP to the test tube.
4. Cover the test tube and briefly vortex mix.
5. Incubate the tube at 37° C. for 25 minutes.
6. Decant the supernatant liquid form each tube after separating magnetic beads using an appropriate magnetic base (e.g., magnetic bar or magnetic holder).
7. Wash the magnetic beads using washing buffer and the magnetic base. Repeat additional times
8. Add 250 µl of 30 µM FDP or 70 µM MUP to the test tube.
9. Cover the tube and briefly vortex mix.
10. Incubate the tube at 37° C. with shaking slowly for 10 minutes for FDP or 20 minutes for MUP in the dark.
11. Transfer the solution (250 µl) to a 0.5 ml centrifuge tube after the separation of magnetic beads using the magnetic base.
12. Pipette 10 µl of working solution into the assigned test tube (12×75 mm) or strip well. Store the rest in the 0.5 ml centrifuge tube in a refrigerator (4° C.).
13. Insert the test tube into a luminometer or the strip well into a microplate luminometer.
14. Read (integration time: 0.5 seconds) CL emitted when OD4MI and $H_2O_2$ are added into the test tube or strip well through two dispensers.

Figure 4:
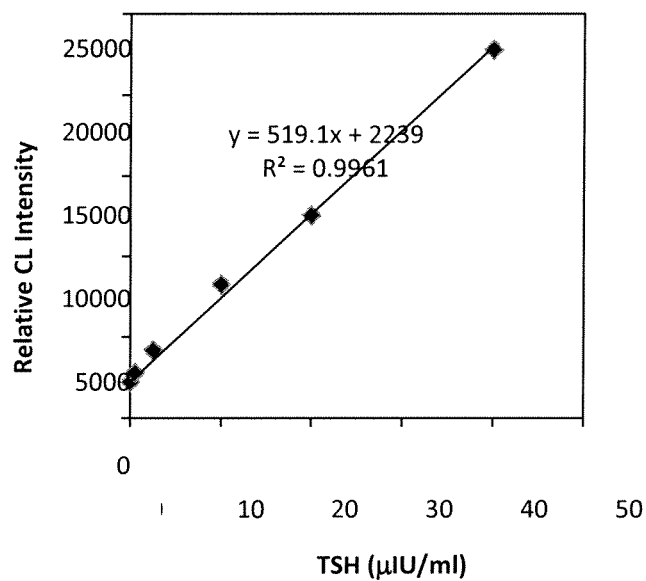
FIG. 4 shows a calibration curve to quantify total TSH in CLEIA using TSH detection antibody-ALP conjugate, 30 µM FDP, and OD4MI CL detection.

As shown in FIG. 4, the calibration curve having good $R^2$ was obtained under the wide concentration range of TSH in OD4MI CLEIA with 30 µM FDP as a substrate. The dynamic range (0.5~40 µIU/ml) of CLEIA capable of quantifying TSH using ALP and OD4MI CL detection (FIG. 4) was the same as that capable of quantifying T4 using HRP and OD4MI CL detection (FIG. 3). However, the LOD (0.11 µIU/ml) of the former was 2.2 times higher than that (0.05 µIU/ml) of the latter. Also, the optimum incubation time between TSH detection antibody-linked ALP and FDP shown in FIG. 4 was 6.7 times longer than the optimum incubation time between TSH detection antibody-conjugated ALP and Amplex Red in the presence of $H_2O_2$ shown in FIG. 2. This is because that relative CL intensity shown in FIG. 4 is lower than that shown in FIG. 2, whereas the background noise in FIG. 4 is higher than that in FIG. 2.

MUP instead of FDP was applied as a substrate in OD4MI CLEIA capable of quantifying TSH. The dynamic range (2.5~40 µIU/ml) to quantify TSH in OD4MI CLEIA using 70 µM MUP as a substrate was shorter than that (0.5~40 µIU/ml) using 30 µM FDP. This is because the CL quantum efficiency of 4-methylumbelliferone formed from the reaction between TSH detection antibody-ALP and MUP is lower than that of fluorescein formed from the reaction between TSH detection antibody-ALP conjugate and FDP.

According to the experimental results, FDP and MUP can be applied as substrates in OD4MI CLEIA to quantify analyte-ALP conjugate. This indicates that other commercialized substrates (e.g., 9H-(1,3-dichloro-9,9-dimethylacridin-2-one-7-yl) phosphate, diammonium salt (DDAO phosphate, 6,8-Difluoro-4-methylumbelliferyl phosphate DiFMUP), Resorufin-7-O-phosphate, diammonium salt (Res-Phos)) capable of reacting analyte-ALP conjugate to produce fluorescence compounds (Dimethylacridinone (DDAO), 6,8-difluoro-4-methylumbelliferone, Resorufin) can also be used as substrates. Also, the sensitivity of OD4MI CLEIA is dependent on the CL quantum efficiency of a fluorescence compound formed from the reaction between an analyte-ALP conjugate and a substrate.

Example 3

Quantification of $H_2O_2$ for the Analyses of Various Enzymes Using HRP and Substrates Used in ODI or ODB CL Quantification of Glucose Using HRP and Amplex Red

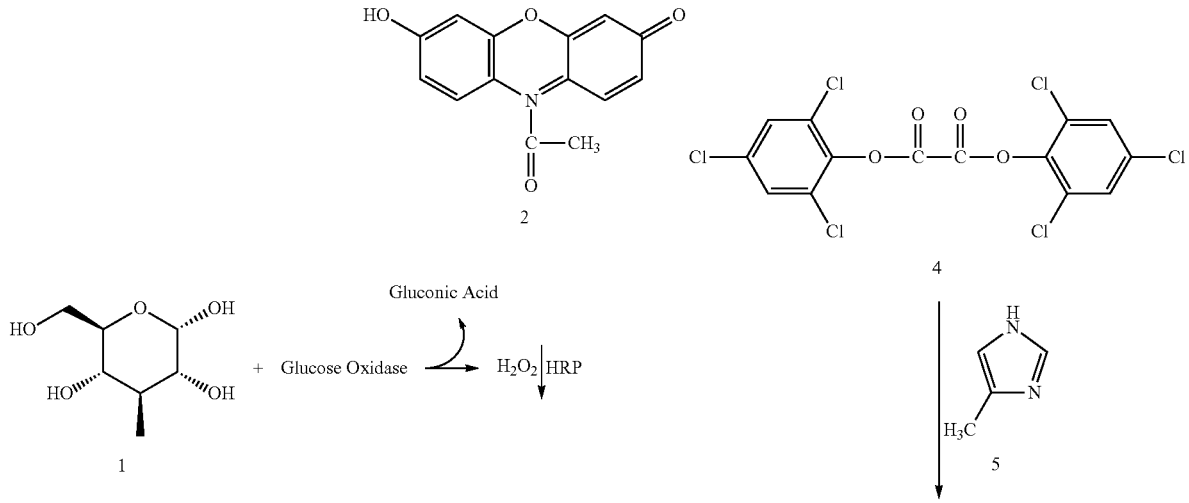

Scheme 5 Reaction mechanism for the quantification of glucose in human serum.

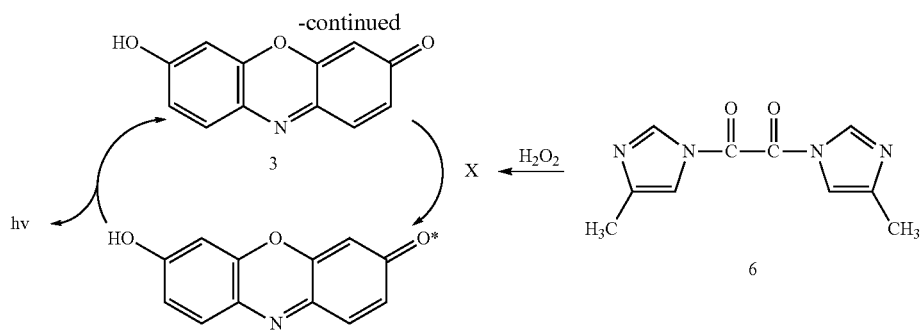

1. Glucose, 2. Amplex Red, 3. Resorufin, 4. TCPO, 5. 4MImH, 6. ODI, X. High-energy intermediate As shown in Scheme 5, $H_2O_2$ is formed from the reaction of glucose and glucose oxidase. $H_2O_2$ formed in this reaction reacts with Amplex Red in the presence of HRP to produce resorufin. Resorufin emits light with the addition of OD4MI CL reagents as shown in Scheme 5. In conclusion, the brightness of CL is proportional to the concentration of glucose.

Preparation 8 different glucose serum samples (0, 0.44, 0.88, 1.75, 3.50, 7.00, 14.00, 28.00) were used as standard samples.

50 µM Amplex Red reagent containing 2.0 mM $H_2O_2$ in deionized water were prepared as described in Example 1 (A).

As another substrate for ODI derivative CL, 0.25 mg/ml OPDA containing 20 mM $H_2O_2$ in deionized water was prepared.

OD4MI was formed from the reaction between 5.0 µM TCPO and 10.0 µM 4-Methylimidazole (4MImH) in Ethyl acetate. 100 mM $H_2O_2$ was prepared in Isopropyl alcohol.

As another CL reagent, 1,1'-oxalyldisodium benzoate (ODB) derivatives (e.g., 1,1'-oxalyldi-2-sodiumbenzoate (OD2B), 1,1'-oxalyldi-4-sodiumbenzoate (OD4B)) were formed from the reaction between 0.5 mM TCPO and 1.0 mM 2-hydroxybenzoic acid sodium salt or 4-Hydroxybenzoic acid sodium salt in Ethyl acetate. 100 mM $H_2O_2$ was prepared in Isopropyl alcohol.

Procedure

1. Various concentrations of glucose (0~28.0 µM) in deionized water containing standard human serum were prepared as standard solutions using 0.54 M stock solution.
2. Human serum samples were diluted 1600 times in deionized water.
3. 4.7 µml glucose oxidase (GO) were prepared in sodium phosphate buffer (pH 7.0).
4. 0.8 U/ml horseradish peroxidase (HRP) was prepared in deionized water.
5. 4.0 mM Amplex Red was prepared in DMSO.
6. 100 µl of HRP (0.8 U/ml) and 50 µl of Amplex Red (4.0 mM) were mixed with 4.85 ml deionized water in a 20-ml vial.
7. 50 µl of GO (4.7 U/ml) and 50 µl of the mixture of HRP and Amplex Red were added in strip-wells.
8. Each 100 µl of standard or sample solution was added in a strip-well containing GO, HRP, and AR.
9. The strip-wells containing glucose, GO, HRP, and Amplex Red were incubated for 15 minutes at room temperature.
10. 10 µl of solution in each strip-well was transferred into a 7.5×12.0 ml test tube.
11. The test tube was inserted into LB Lumat Luminometer (Berthold Inc.).
12. When the start button of the luminometer was pressed, the test tube moved to the detection area. Then 25 µl of ODI in ethyl acetate and 25 µl of $H_2O_2$ in isopropyl alcohol were injected into the test tube using two dispensers.
13. Finally, CL light emitted in the test tube was measured for 0.5 second.

Figure 5:
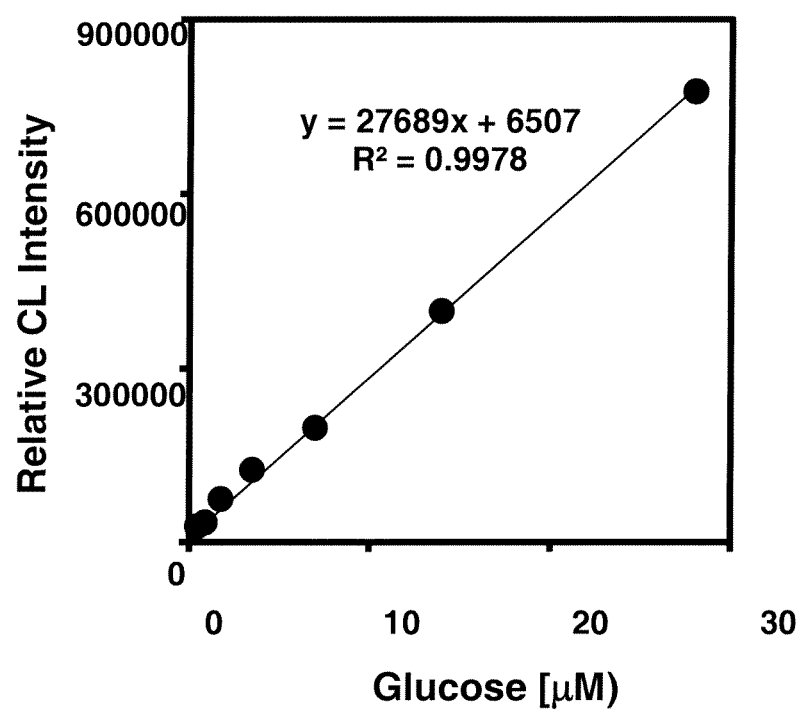
FIG. 5 shows a calibration curve for the quantification of $H_2O_2$ in human serum.

As shown in FIG. 5, a wide linear calibration curve (0.43~28.0 µM) capable of quantifying glucose in human serum was obtained. LOD and LOQ of the method for the quantification of glucose were 0.11 and 0.36 µM, respectively. Thus, the sensitivity of the analytical method with ODI CL detection was at least 10 times better than that of other techniques with absorbance, electrochemical and fluorescence.

TABLE 3

Intra-assay and inter-assay for the quantification of glucose in human serum

| | Intra-assay (n = 7)[1] | | Inter-assay (n = 24)[2] | |
|---|---|---|---|---|
| | Concentration[1] | CV (%)[2] | Concentration[1] | CV (%)[2] |
| 1 | 7.30 | 2.2 | 7.46 | 4.3 |
| 2 | 7.23 | 6.3 | 7.52 | 4.9 |
| 3 | 15.46 | 2.1 | 15.77 | 3.5 |
| 4 | 12.15 | 2.7 | 12.09 | 3.3 |
| 5 | 8.94 | 2.4 | 9.01 | 4.4 |

[1]The experiment for each sample was repeated 7 times.
[2]The experiment for each sample was repeated 3 times every day for 8 days.
[3]µM
[4]Confidence of variable The results of intra-assay and inter-assay shown in Table 3 indicate that the new biosensor can quantify trace levels of glucose in human serum with excellent accuracy and precision.

2,3-diaminopherazine (DAPN) is formed when $H_2O_2$ reacts with OPDA in the presence of HRP. The fluorescent product DAPN is excited when high-energy intermediate, formed from the reaction between OD4MI and $H_2O_2$, transfers energy to DAPN. And then, the excited DAPN emits strong CL (see Scheme 1). Thus, low concentration of glucose in human serum was determined using OD4MI CL. A calibration curve in the range of 0.43~28 µM ($R^2$=0.994) was obtained. However, the LOD (0.34 µM) determined with OPDA was not as good as that (0.11 µM) determined with Amplex Red. This is because quantum efficiency of OPDA is lower than that of Amplex Red.

Using OD4B instead of ODI derivatives, low concentration of glucose was quantified. Relative CL intensity measured in OD4B CL detection was 10 times lower than that measured in ODI derivative CL detection even though the concentration of TCPO used to produce OD4B were 100 times higher than that used to form ODI. However, the background noise of the former was about 20 times lower than that of the latter. Due to the properties of OD4B CL, the integration time (2 seconds) of light emitted in OD4B CL was 4 times longer than that emitted in OD4MI CL. Based on the experimental condition of OD4B CL, the LOD (0.14 µIU/ml) and dynamic range (0.43~28.00 µM, $R^2$=0.996) determined with ODB derivative CL detection were similar to or the same as those obtained with ODI derivative CL detection within the statistical error range (95% confidence interval).

The sensitivity of ODB derivative CL detection was dependent on the properties of ODB derivatives. The LOD of OD4B CL detection was about 3 times lower than that of OD2B CL detection.

In conclusion, the results shown in examples for the quantification of glucose indicate that various enzymes in a human sample can be quantified as the concentration of $H_2O_2$ formed when one of these enzymes reacts with a specific enzyme oxidase is determined using HRP, a substrate (e.g., Amplex Red, DAPN), and a CL detection (e.g., ODI derivative CL, ODB derivative CL). Non-limited examples of the various enzymes include acetylcholine, catalase, cholesterol, choline, galactose, glucose, glutamine, phosphate, uric acid.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention. Thus, the breadth and scope of the invention should not be limited by any of the above-described exemplary embodiments.

What is claimed is:

1. A method of quantifying antigen or antibody-labeled enzymes, comprising:
    adding 1,1'-Oxalyldi-4-methyl-imidazole (OD4MI) to a chemiluminescent immunoassay comprising the antigen or antibody-labeled enzyme to be quantified, wherein the addition occurs in aqueous solution; and
    correlating chemiluminescence emission intensity to antigen or antibody-labeled enzyme quantity.

2. The method of claim 1, wherein the correlating step is accomplished by plotting a calibration curve based on sample concentration on the x-axis and chemiluminescence intensity on the y-axis, wherein concentration of the sample is determined using the calibration curve and chemiluminescence emission measured in each test sample.

* * * * *